United States Patent [19]

Dennis

[11] Patent Number: 5,518,907
[45] Date of Patent: May 21, 1996

[54] **CLONING AND EXPRESSION IN *ESCHERICHIA COLI* OF THE *ALCALIGENES EUTROPHUS* H16 POLY-BETA-HYDROXYBUTYRATE BIOSYNTHETIC PATHWAY**

[75] Inventor: Douglas E. Dennis, Weyers Cave, Va.

[73] Assignee: Center for Innovative Technology, Herndon, Va.

[21] Appl. No.: 252,049

[22] Filed: May 31, 1994

Related U.S. Application Data

[63] Continuation of Ser. No. 362,514, Jun. 7, 1989, abandoned.
[51] Int. Cl.[6] .............................. C12P 21/06; C12P 7/52; C12N 15/00; C12N 1/20
[52] U.S. Cl. .................. 435/141; 435/172.3; 435/252.33; 435/69.1
[58] Field of Search ................................ 435/69.1, 141, 435/172.3, 252.33

[56] References Cited

U.S. PATENT DOCUMENTS

| | | | |
|---|---|---|---|
| 2,811,511 | 10/1957 | Alderson . | |
| 3,021,309 | 2/1962 | Cox et al. . | |
| 3,036,959 | 5/1962 | Baptist | 195/47 |
| 3,044,942 | 7/1962 | Baptist | 195/47 |
| 3,107,172 | 10/1963 | Baptist et al. . | |
| 3,121,669 | 2/1964 | Baptist | 195/47 |
| 3,275,610 | 9/1966 | Coty . | |
| 3,293,225 | 12/1966 | Wakasa et al. . | |
| 3,314,801 | 4/1967 | Cadmus et al. . | |
| 3,406,114 | 10/1968 | Goren et al. . | |
| 3,553,081 | 1/1971 | Goodhue et al. | 195/30 |
| 3,579,549 | 5/1971 | Stockman et al. . | |
| 3,624,047 | 11/1971 | Ogawa et al. . | |
| 3,632,570 | 1/1972 | Gill . | |
| 3,806,495 | 4/1974 | Schoen . | |
| 3,923,782 | 12/1975 | Finn et al. . | |
| 4,101,533 | 7/1978 | Lafferty et al. | 528/491 |
| 4,138,291 | 2/1979 | Lafferty | 195/47 |
| 4,140,741 | 2/1979 | Lafferty et al. | 264/184 |
| 4,211,846 | 7/1980 | Lafferty | 435/141 |
| 4,237,224 | 12/1980 | Cohen et al. | 435/172.3 |
| 4,306,026 | 12/1981 | Maslen et al. . | |
| 4,310,684 | 1/1982 | Vanlautem et al. | 560/185 |
| 4,324,880 | 4/1982 | Dhein et al. . | |
| 4,324,907 | 4/1982 | Senior et al. | 560/185 |
| 4,326,035 | 4/1982 | Gabellieri | 435/247 |
| 4,329,448 | 5/1982 | Cox et al. | 536/123 |
| 4,336,334 | 6/1982 | Powell et al. | 435/146 |
| 4,337,181 | 6/1982 | Otey et al. | 523/128 |
| 4,358,583 | 11/1982 | Walker et al. | 528/491 |
| 4,360,488 | 11/1982 | Barham et al. . | |
| 4,365,088 | 12/1982 | Vanlautem et al. . | |
| 4,385,026 | 5/1983 | Barham . | |
| 4,391,766 | 7/1983 | Barham et al. | 264/210.1 |
| 4,394,447 | 7/1983 | Cadmus et al. . | |
| 4,396,763 | 8/1983 | Tsuchiya et al. . | |
| 4,427,614 | 1/1984 | Barham et al. | 264/210.1 |
| 4,433,053 | 2/1984 | Hughes et al. | 435/141 |
| 4,477,654 | 10/1984 | Holmes et al. | 528/361 |
| 4,477,655 | 10/1984 | Holmes | 528/361 |
| 4,487,835 | 12/1984 | Uhlin et al. . | |
| 4,491,575 | 1/1985 | Korsatko | 424/19 |
| 4,495,287 | 1/1985 | Uhlin et al. . | |
| 4,499,189 | 2/1985 | Uhlin et al. . | |
| 4,503,155 | 3/1985 | Miller et al. | 435/172.3 |

(List continued on next page.)

FOREIGN PATENT DOCUMENTS

| | | |
|---|---|---|
| 0036699B2 | 9/1981 | European Pat. Off. . |
| 0046017A3 | 2/1982 | European Pat. Off. . |
| 0046344A3 | 2/1982 | European Pat. Off. . |
| 0052459B1 | 5/1982 | European Pat. Off. . |
| 0052460A1 | 5/1982 | European Pat. Off. . |
| 0069497A2 | 1/1983 | European Pat. Off. . |
| 0078609B1 | 5/1983 | European Pat. Off. . |
| 0093021A2 | 11/1983 | European Pat. Off. . |
| 0104731B1 | 4/1984 | European Pat. Off. . |
| 0114086A2 | 7/1984 | European Pat. Off. . |
| 0145233A2 | 6/1985 | European Pat. Off. . |
| 0149744B1 | 7/1985 | European Pat. Off. . |
| 0168095A1 | 1/1986 | European Pat. Off. . |
| 0204442A2 | 12/1986 | European Pat. Off. . |
| 0288908A2 | 11/1988 | European Pat. Off. . |
| 0355307A2 | 2/1990 | European Pat. Off. . |
| 0432443A1 | 6/1991 | European Pat. Off. . |
| 0431883A2 | 6/1991 | European Pat. Off. . |
| 0435028A2 | 7/1991 | European Pat. Off. . |
| 0440165A2 | 8/1991 | European Pat. Off. . |
| 0466050A1 | 1/1992 | European Pat. Off. . |
| 0476785A2 | 3/1992 | European Pat. Off. . |
| 229428A1 | 11/1985 | German Dem. Rep. . |
| 239609A1 | 10/1986 | German Dem. Rep. . |
| 276304A1 | 2/1990 | German Dem. Rep. . |
| 3937649A1 | 5/1991 | Germany . |

(List continued on next page.)

OTHER PUBLICATIONS

Slater et al., "Cloning and Expression in *Escherichia coli* of *Alcaligenes eutrophus* H16 Poly–Beta–Hydroxybutyrate Biosynthetic Pathway" Oct., 1988, Journal of Bacteriology, pp. 4431–4436.

Schubert et al., "Cloning of the *Alcaligenes eutrophus* Genes for Synthesis of Poly–Beta–Hydroxybutyric Acid (PHB) and Synthesis of PHB in *Escherichia coli*," Dec., 1988, Journal of Bacteriology, vol. 170, No. 11, pp. 5837–5847.

Peoples et al., "BiosyntheticThiolase from *Zoogloea ramigera*: III. Isolation and characterization of the structural gene," Jan. 5, 1987, The Journal of BiologicalChemistry, vol. 262, No. 1, pp. 97–102.

(List continued on next page.)

*Primary Examiner*—Robert A. Wax
*Assistant Examiner*—Hyosuk Kim
*Attorney, Agent, or Firm*—Seed and Berry

[57] ABSTRACT

Genes coding for poly-beta-hydroxybutyrate were removed from *Alcaligenes eutrophus* H16 and cloned into *Escherichia coli*. Some of the clones produced PHB to 90% of the cell weight.

8 Claims, 7 Drawing Sheets

U.S. PATENT DOCUMENTS

| | | | |
|---|---|---|---|
| 4,508,823 | 4/1985 | Olsen . | |
| 4,529,797 | 7/1985 | Peik et al. . | |
| 4,537,738 | 8/1985 | Holmes | 264/210.5 |
| 4,562,245 | 12/1985 | Stageman | 528/361 |
| 4,567,140 | 1/1986 | Voelskow et al. . | |
| 4,575,551 | 3/1986 | Fujiyama et al. . | |
| 4,599,311 | 7/1986 | Kawasaki . | |
| 4,603,070 | 7/1986 | Steel et al. | 428/88 |
| 4,620,999 | 11/1986 | Holmes | 428/35 |
| 4,626,504 | 12/1986 | Puhler et al. | 435/172.3 |
| 4,631,259 | 12/1986 | Clewell et al. . | |
| 4,638,059 | 1/1987 | Sutherland . | |
| 4,647,657 | 3/1987 | Wan . | |
| 4,705,604 | 11/1987 | Vanlautem et al. | 203/67 |
| 4,711,848 | 12/1987 | Insley et al. . | |
| 4,713,449 | 12/1987 | Vanderslice et al. . | |
| 4,743,453 | 3/1988 | Ahern et al. . | |
| 4,752,580 | 6/1988 | Downs . | |
| 4,758,356 | 7/1988 | Downs . | |
| 4,760,022 | 7/1988 | Molin et al. . | |
| 4,786,598 | 11/1988 | Lafferty et al. | 435/146 |
| 4,806,471 | 2/1989 | Molin et al. . | |
| 4,806,482 | 2/1989 | Horowitz | 435/262 |
| 4,826,945 | 5/1989 | Cohn et al. . | |
| 4,876,331 | 10/1989 | Doi | 528/361 |
| 4,900,299 | 2/1990 | Webb | 604/11 |
| 4,902,516 | 2/1990 | Korsatko et al. | 424/497 |
| 4,910,145 | 3/1990 | Holmes et al. | 435/259 |
| 4,948,733 | 8/1990 | Easson, Jr. et al. | 435/172.3 |
| 4,950,749 | 8/1990 | Johal et al. . | |
| 4,952,496 | 8/1990 | Studier et al. | 435/91 |
| 4,957,861 | 9/1990 | Lafferty et al. | 435/146 |
| 4,960,866 | 10/1990 | Bendix et al. . | |
| 4,965,197 | 10/1990 | Liebl et al. | 435/69.8 |
| 4,968,611 | 11/1990 | Traussnig et al. | 435/135 |
| 4,992,540 | 2/1991 | Jamas et al. . | |
| 4,997,909 | 3/1991 | Doi . | |
| 5,004,664 | 4/1991 | Fuller et al. . | |
| 5,008,108 | 4/1991 | Rha et al. . | |
| 5,028,703 | 7/1991 | Jamas et al. . | |
| 5,032,512 | 7/1991 | Witholt et al. . | |
| 5,037,972 | 8/1991 | Jamas et al. . | |
| 5,059,536 | 10/1991 | Page et al. . | |
| 5,076,983 | 12/1991 | Loomis et al. . | |
| 5,082,936 | 1/1992 | Jamas et al. . | |
| 5,091,376 | 2/1992 | Easson, Jr. et al. . | |
| 5,096,819 | 3/1992 | Page et al. . | |
| 5,107,016 | 4/1992 | Pennetreau . | |
| 5,110,852 | 5/1992 | Gogolewski et al. . | |
| 5,110,980 | 5/1992 | Ramsay et al. . | |
| 5,124,371 | 6/1992 | Tokiwa et al. . | |
| 5,126,255 | 6/1992 | Anderson et al. . | |
| 5,135,859 | 8/1992 | Witholt et al. . | |
| 5,138,029 | 8/1992 | Nishioka et al. . | |
| 5,229,279 | 7/1993 | Peoples et al. | 435/135 |

FOREIGN PATENT DOCUMENTS

| | | |
|---|---|---|
| 290914A5 | 6/1991 | Germany . |
| 4003827A1 | 8/1991 | Germany . |
| 294280A5 | 9/1991 | Germany . |
| 4036067A1 | 5/1992 | Germany . |
| 61-45778 | 9/1987 | Japan . |
| 63-198991 | 8/1988 | Japan . |
| 62-103228 | 11/1988 | Japan . |
| 62183260 | 1/1989 | Japan . |
| 1-27483 | 1/1989 | Japan . |
| 62204537 | 2/1989 | Japan . |
| 62204538 | 2/1989 | Japan . |
| 2-234683 | 3/1989 | Japan . |
| 62224083 | 3/1989 | Japan . |
| 63-49015 | 9/1989 | Japan . |
| 1-304891 | 12/1989 | Japan . |
| 63-136748 | 12/1989 | Japan . |
| 3-143397 | 6/1991 | Japan . |
| 3-216193 | 9/1991 | Japan . |
| 3-277628 | 12/1991 | Japan . |
| 2089823 | 6/1982 | United Kingdom . |
| 2120671 | 12/1983 | United Kingdom . |
| 2180540 | 1/1987 | United Kingdom . |
| WO8607608 | 12/1986 | WIPO . |
| WO90/12104 | 10/1990 | WIPO . |
| WO9100917 | 1/1991 | WIPO . |
| WO91/18995 | 12/1991 | WIPO . |

OTHER PUBLICATIONS

Peoples et al,. "Fine structural analysis of the *Zooglea ramigera* phbA-phbB locus encoding Beta-ketothiolase and acetoacetyl-CoA reductase: nucleotide sequence of phbB," Mar. 1989, Molecular Microbiology, vol. 3, #3, pp. 349-357.

Ballard, et. al. in *Recent Advances in Mechanistic and Synthetic Aspects Of Polymerization;* Fontanille, et al. (eds.); D. Reidel Publishing Company, Dordrecht Holland; pp. 293-314 1987.

Slater, et. al., Am. Soc. Of Microbiology, Annual Mtg., Abstract H-123, Mar. 1-6, 1987.

Johnson, et. al., Virginia J. of Science, p. 150, May 19-22, 1987.

Slater, et. al., Virginia J. of Science, p. 152, May 19-22, 1987.

Byrom Polymer Synthesis By Microorganisms: Technology And Economics. Trends In Biotechnology, vol. 5, pp. 246-250 1987.

Ploux, et. al. The NADPH-Linked Acetoacetyl-CoA Reductase From *Zoogloea ramigera* European J. Biochem., vol. 174, pp. 177-182 1988.

Pub. #PCT/WO89/00202, Peoples et al. Jan. 12, 1989.

Pub. #PCT/WO88/00948, Sinskey et al. Feb. 11, 1988.

Pub. #PCT/WO90/10671, Bastioli et al. Sep. 20, 1990.

Pub. #PCT/WO90/01043, Tomka Feb. 8, 1990.

Reusch et al., Federation of American Societies for Experimental Biology 72nd Annual Meeting; abstract #8504, 1-5 May, 1988.

Doi, Yoshiharu, et al., Makromol. Chem. Rapid Commun. 10:227-230, May 1989.

Brandl, Helmut et al., Int. J. Biol. Macromol., 11:4955, Feb. 1989.

Arnold, Steven C., et al., Makromol. Chem., Macromol. Symp. 6, 285-303, Dec. 1986.

Gross, Richard A., et al., Polym. Prepr. (AM. Chem. Soc., Div. Polym. (Chem.) 1988, 29:596-7.

Fuller, R. C., et al., Massachusetts Univ., Amherst Dept. of Biochemistry, Journal vol. 08915; Annual Rept. 1 Mar. 88-22 Feb. 89.

NERAC Inc., Copyright 1990; Oct. 3, 1990, pp. 1-18 & pp. 1-60; "Tech Track Update: Bacteria-Produced Biopolymers".

*Genetic Technology News,* vol. 9, No. 9, Sep. 1989, p. 5.

Peoples et al., Molecular Biology, 3:349-359, 1989.

Haywood et al,. FEMS Microbiology Letters, 52:91-96, 1988.

Haywood et al., FEMS Microbiology Letter, 52:259-264, 1988.

Reusch et al., Journal of Bacteriology, 168:553-562, Nov. 1986.

Chemical Week, Aug. 28, 1985.

Ayres et al., *Microbiology of Foods*, W. H. Freeman & Company, San Francisco, 1980, pp. 191–192.

Schubert et al., "Molecular Analysis of the *Alcaligenes eutrophus* Poly(3–Hydroxybutyrate) Biosynthetic Operon: Identification of the N Terminus of Poly(3–Hydroxybutyrate) Synthase and Identification of the Promoter", J. Bacteriol., 173:168–175, Jan. 1991.

Peoples et al., "Poly–β–hydroxybutyrate (PHB) Biosynthesis in *Alcaligenes eutrophus* H16: Identification and Characterization of the PHB Polymerase Gene (phbC)", J. Bio. Chem., 264:15298–15303, Sep. 1989.

Peoples et al., "Poly–β–hydroxybutyrate Biosynthesis in *Alcaligenes eutrophus* H16: Characterization of the Genes Encoding β–ketothiolase and Acetoacetyl–CoA Reductase", J. Bio. Chem., 264:15293–15297, Sep. 1989.

Doi et al., "Biodegradation of Microbial Copolyesters: Poly(3–hydroxybutyrate–co–3–hydroxyvalerate) and Poly(3–hydroxybutyrate–co–4–hydroxybutyrate)", Macromolecules, 23:26–31, 1990.

Computer Search—Miscellaneous Abstracts, pp. 1–60.

Steinbuchel et al., "Expression of the *Alcaligenes eutrophus* poly(β–hydroxybutyric acid)—synthetic pathway in Pseudomas sp.", Microbiol., 153:101–104, 1989.

Keeler, "Plastics Grown in Bacteria Inch Toward the Market", *R & D Magazine*, pp. 46–52, Jan. 1991.

Pool, "One Word, Son: Bugs", *Discover*, pp. 22–23, Jul. 1990.

Dawes, "Aspects of the Regulation of Polyhydroxyalkanoate Metabolism", *International Symposium on Biodegradable Polymers*, pp. 85–89, Oct. 29–31, 1990.

Fuller et al., "Biosynthesis and Biodegradation of Polyesters", *International Symposium on Biodegradable Polymers*, pp. 90–93; Oct. 29–31, 1990.

Doi, "Production and Biodegradation of Microbial Copolyesters", *International Symposium on Biodegradable Polymers*, pp. 94–98; Oct. 29–31, 1990.

Peoples et al., "Genes to PHA Polymers", *International Symposium on Biodegradable Polymers*, p. 108; Oct. 29–31, 1990.

Steinbuchel et al., "Molecular Analysis of Genes Essential for and Affecting the Synthesis of Poly(β–Hydroxyalkanoates) in *Alcaligenes eutrophus*", *International Symposium on Biodegradable Polymers*, pp. 109–113, Oct. 29–31, 1990.

Endo et al., "Preparation of Functional Poly(amino acid) and Their Application to Biodegradable Polymers", *International Symposium on Biodegradable Polymers*, pp. 114–118; Oct. 29–31, 1990.

Kalousek et al., "Release of Poly–β–hydroxybutyrate Granules from *Escherichia coli* by Protein E–mediated Lysis", *International Symposium on Biodegradable Polymers*, p. 150; Oct. 29–31, 1990.

Kawaguchi et al., "In Vivo $^{13}$C NMR Analysis of Poly(3–hydroxybutyrate) and Trehalose Metabolism in *Alcaligenes eutrophus*", *International Symposium on Biodegradable Polymers*, p. 151; Oct. 29–31, 1990.

Nakamura et al., "Biosynthesis of Biodegradable Copolyesters by *Alcaligenes eutrophus* from Various Carbon Substrates", *International Symposium on Biodegradable Polymers*, p. 152; Oct. 29–31, 1990.

Koyama et al., "One–stage production of P(3–hydroxybutyrate–co–3–hydroxyvalerate) by *Alcaligenes eutrophus* in fed batch culture", *International Symposium on Biodegradable Polymers*, p. 153; Oct. 29–31, 1990.

Liebergesell et al., "Cloning of the Genes for Poly(β–Hydroxybutyric Acid) Synthesis of *Chromatium vinosum*", *International Symposium on Biodegradable Polymers*, p. 178, Oct. 29–31, 1990.

Hrabak, "Development of a New Production Process for PHB", *International Symposium on Biodegradable Polymers*, p. unknown, Oct. 29–31, 1990.

Steinbuchel et al., "Genetic and Molecular Analysis of the *Alcaligenes eutrophus* Polyhydroxyalkanoate–Biosynthetic Genes and Accumulation of PHA in Recombinant Bacteria", *Novel Biodegradable Microbial Polymers* (E. A. Dawes, Ed.), pp. 143–159, 1990.

Witholt et al., "Bacterial Poly(3–Hydroxyalkanoates)", *Novel Biodegradable Microbial Polymers* (E. A. Dawes, Ed.), pp. 161–173, 1990.

Huisman, "Metabolism of Poly(3–hydroxyalkanoates) (PHAs) by *Pseudomonas oleovorans*", J. Bio. Chem., 266:2191–2198, Feb. 5, 1991.

Doi et al., "Biosynthesis and characterization of poly(3–hydroxybutyrate–co–4–hydroxybutyrate) in *Alcaligenes eutrophus*", Int. J. Biol. Macromol., 12:106–111, Apr. 1990.

Capon et al., "Poly–3–Hydroxyalkanoates from Marine and Freshwater Cyanobacteria", Phytochemistry, 22:1181–1184, 1983.

Doi, *Microbial Poly(hydroxyalkanoates)*, pp. 4–6, book.

Janes et al., "Molecular Characterization of the Poly–β–Hydroxybutyrate Biosynthetic Pathway of *Alcaligenes eutrophus* H16", *Novel Biodegradable Microbial Polymers* (E. A. Dawes, Ed.), pp. 175–190, 1990.

Smith et al., *Principles of Biochemistry: General Aspects*, McGraw–Hill, 1983, p. 53.

Sheeler et al., *Cell and Molecular Biology*, Third Edition, John Wiley & Sons, 1987, p. 284.

Studier et al., "Use of T7 RNA Polymerase to Direct Expression of Cloned Genes", *Methods in Enzymology*, 185:60–89, 1990.

Poirer et al., "Polyhydroxybutyrate, a Biodegradable Thermoplastic, Produced in Transgenic Plants", Science, 256:520–523, Apr. 24, 1992.

Findlay et al., "Polymeric Beta–Hydroxyalkanoates from Environmental Samples and *Bacillus megaterium*", Applied and Environ. Microbiol., 45:71–78, 1983.

Oldham et al., "Combined Determination of Poly–β–Hydroxyalkanoic and Cellular Fatty Acids in Starved Marine Bacteria and Sewage Sludge by Gas Chromatography with Flame Ionization of Mass Spectrometry Detection", Applied and Environ. Microbiol., 52:905–910, 1986.

Alfred Benson, Inc., brochure, *Runaway Replication Plasmid Technology* (RAP™). (1988).

Wallen et al., "Biopolymers of Activated Sludge", Environmental Science & Technology, 6:161–164, Feb. 2, 1972.

Wallen et al., "Poly–β–hydroxyalkanoate from Activated Sludge", Environmental Science & Technology, 8:576–579, Jun. 6, 1974.

Davis, "Cellular Lipids of a Nocardia Grown on Propane and n–Butane", Applied Microbiology, 12:301–304, Jul. 1964.Marchessault et al., "Physical Properties of Poly–β–Hydroxyvalerate: a Natural Chiral Polyalkanoate", IUPAC Macro Florence 1980: International Symposium on Macromoles preprints, 2:272–276, 1980.

Morikawa et al., "Pyrolysis of bacterial polyalkanoates", Canadian J. Chem., 59:2306–2313, 1981.

Ditta et al., "Broad host range DNA cloning system for Gram–negative bacteria: construction of a gene bank of *Rhizobium meliloti*", *Proc. Natl. Acad. Sci.*, 77(12), 7347–7351, Dec. 1980.

Farrah et al., "Isolation of Exocellular Polymer from Zoogloea Strains MP6 and 106 and from Activated Sludge", *Applied and Environ. Microbiol.*, 32(1), 33–37, Jul. 1976.

Ish–Horowicz, "Rapid and efficient cosmid cloning", *Nucleic Acids Research*, 9(13), 2989–2998, Jul. 10, 1981.

Okita et al., "Biosynthesis of Bacterial Glycogen", J. Biol. Chem., 256:6944–6952, 1981.

Parsons et al., "Production of Extracellular Polysaccharide Matrix by *Zoogloea ramigera*", *Applied Microbiology*, 21(4), 657–661, Apr. 1971.

Sinskey et al., "Biopolymers and Modified Polysaccharides", *Biotechnology in Food Processing*, 1986.

Stauffer et al., "Characterization of Zooglan–115, an Exocellular Glycan of *Zoogloea ramigera*–115", J. Food Sci., 45:746–952, 1980.

Norberg et al., "Production of Extracellular Polysaccharide by *Zoogloea ramigera*", Applied and Environ. Microbiol., 44:1231–1237, 1982.

Darzins et al., "Cloning of Genes Controlling Alginate Biosynthesis from a Mucoid Cystic Fibrosis Isolate of *Pseudomonas aeruginosa*", J. Bacteriol., vol. 159(1), pp. 9–18, 1984.

Cooper et al., "Production of Exopolysacchardies from Lactose by Wildtype *Zoogloea ramigera* and a Capsule Minus Mutant Strain Isolated by Buoyant Density Centrifugation", Abstract Production of Exopolysaccharides . . . , Dept. Chem. Eng., University of Wisconsin. Am. Chem. Soc. v. 198 (1989).

Okayama et al., "Bacteriophage Lambda Vector for Transducing a cDNA Clone Library into Mammalian Cells", Mol. and Cell. Biol., 5:1136–1142, 1985.

Computer Search of Ramigera and Gene.

Analysis of cosmid clones for enzyme activity and PHB accumulation

| Bacterium[a] | Cosmid | β-Ketothiolase activity[b] | Acetoacetyl-CoA reductase activity[c] | mg of PHB/ml of culture | %PHB |
|---|---|---|---|---|---|
| E. coli LE392 | None | 0.0 | 0.0 | 0.0 | 0 |
| A. eutrophus H16 | None | 12.4 | 12.3 | 1.18 | 35 |
| E. coli LE392 | pAE65 | 5.2 | 39.0 | 0.03 | 1 |
| E. coli LE392 | pAE175 | 16.2 | 0.2 | 0.47 | 16 |
| E. coli LE392 | pAE537 | 2.4 | 0.0 | 0.0 | 0 |
| E. coli LE392 | pAE683 | 10.4 | 0.0 | 0.0 | 0 |
| E. coli LE392 | pAE689 | 14.8 | 0.2 | 0.64 | 20 |
| E. coli LE392 | pAE902 | 8.5 | 0.0 | 0.0 | 0 |

[a] Bacteria were grown in LB plus 1% gluconate.
[b] Micromoles of acetoacetyl-CoA degraded per minute per milligram of protein.
[c] Micromoles of NADPH reduced per minute per milligram of protein.

FIG. 2

Analysis of subclones for enzyme activity and PHB production

| Bacterium[a] | Plasmid | β-Ketothiolase activity[b] | Acetoacetyl-CoA reductase activity[c] | mg of PHB/ml of culture | %PHB |
|---|---|---|---|---|---|
| E. coli LE392 | None | 0.0 | 0.0 | 0.0 | 0 |
| A. eutrophus H16 | None | 3.5 | 11.2 | 1.64 | 49 |
| E. coli LE392 | pAE175 | 1.7 | 1.2 | 0.71 | 19 |
| E. coli DH5 | pBK6 | 1.6 | 0.0 | 0.0 | 0 |
| E. coli DH5 | pBK12 | 2.0 | 4.5 | 0.71 | 18 |
| E. coli DH5 | pSB2 | 0.0 | 0.0 | 0.0 | 0 |
| E. coli DH5 | pSB3 | 0.0 | 0.0 | 0.0 | 0 |
| E. coli DH5 | pSB8 | 59.2 | 50.1 | 0.0 | 0 |
| E. coli DH5 | pSB9 | 20.2 | 8.7 | 0.0 | 0 |
| E. coli DH5 | pSB13 | 0.0 | 0.0 | 0.0 | 0 |
| E. coli DH5 | pSB14 | 0.0 | 0.0 | 0.0 | 0 |
| E. coli DH5 | pSB20 | 2.7 | 0.7 | 2.82 | 54 |
| E. coli DH5 | pSB21 | 2.4 | 0.6 | 2.28 | 39 |

[a] For enzyme assays, bacteria were grown in LB. For the PHB assay, bacteria were grown in LB plus 1% gluconate.
[b] Micromoles of acetoacetyl-CoA degraded per minute per milligram of protein.
[c] Micromoles of NADPH reduced per minute per milligram of protein.

FIG. 4

CLONING AND EXPRESSION IN *ESCHERICHIA COLI* OF THE *ALCALIGENES EUTROPHUS* H16 POLY-BETA-HYDROXYBUTYRATE BIOSYNTHETIC PATHWAY

CROSS-REFERENCE TO RELATED APPLICATION

This application is a continuation of U.S. patent application Ser. No. 07/362,514, filed Jun. 7, 1989, now abandoned.

DESCRIPTION

BACKGROUND OF THE INVENTION

1. Field of the Invention

The invention is generally related to recombinant deoxyribonucleic acid (DNA) technology and, more particularly, to cloning the genes responsible for biosynthesis of poly-beta-hydroxybutyrate (PHB) from *Alcaligenes eutrophus* H16 (*A. eutrophus*) into *Escherichia coli* (*E. coli*) and expressing the PHB biosynthetic pathway in *E. coli*.

2. Description of the Prior Art

PHB is an energy storage material produced by a variety of bacteria in response to environmental stress. Lemoigne discovered the presence of PHB in Bacillus in 1926 and it has since been identified in several different bacterial genera, including Azotobacter, Beijerinckia, Alcaligenes, Psuedonomas, Rhizobium, and Rhodospirillum. PHB is a homopolymer of D-(-)-3-hydroxybutyrate and has properties comparable to polypropylene. PHB is commercially produced using *A. eutrophus* and is sold on the market under the tradename Biopol. An exciting feature of PHB relative to other commercially available plastics is its biodegradability which makes it more suitable for packaging purposes since it will not have an adverse environmental impact. PHB has also been used as a source of chiral centers for the organic synthesis of certain antibiotics, and has been utilized in drug delivery and bone replacement applications.

The biosynthesis of PHB has been studied extensively in *A. eutrophus* and *Azotobacter beijerinckii*. FIG. 1 outlines a three step biosynthetic pathway for PHB found in most prokaryotic organisms. Beta-ketothiolase first catalyzes the reversible condensation of two acetyl coenzyme A (CoA) molecules to acetoacetyl-CoA. The acetoacetyl-CoA is reduced by acetoacetyl-CoA reductase to D-(-)-3-hydroxybutyryl-CoA. Enzyme action of the acetoacetyl-CoA reductase is dependent on NADPH. PHB synthetase polymerizes the D-(-)-3-hydroxybutyryl-CoA to PHB.

PHB accumulates when growth of a bacteria culture is restricted by a nutrient other than a carbon source. For example, oxygen deprivation, nitrogen deprivation, sulfate limitation and magnesium limitation have all been used as limitations on environmental conditions. Under such environmental conditions, the PHB content in bacteria cells can increase to as much as 80% of the dry weight. When the limiting conditions are relaxed, PHB quantities decrease to preinduction levels. Induction studies in which beta-ketothiolase and acetoacetyl CoA reductase were studied have revealed that both enzymatic activities increase markedly in response to PHB-stimulating limitation conditions.

Examples of U.S. Patents dealing with the biotechnological production of PHB and extraction of PHB from microorganisms include the following: U.S. Pat. No. 4,786,598 to Lafferty et al. discloses a two stage fermentation process where PHB is produced using *Alcaligenes latus*, U.S. Pat. No. 4,705,604 to Vanlautem et al. discloses using 1,2 dichloroethane to simultaneously remove water from the bacterial suspension by azeotropic distillation and extract PHB from the cells, U.S. Pat. No. 4,477,654 to Holmes et al discloses limiting the nitrogen nutrient source to microbiologically accumulate 3-hydroxybutyrate polymers, U.S. Pat. No. 4,433,053 discloses a fermenting process for PHB accumulation using *A. eutrophus* where a nutrient required for growth is limited, U.S. Pat. No. 4,336,334 to Powell et al. shows a microbiological process for producing PHB using *Methylobacterium organophilum*, U.S. Pat. No. 4,358,583 to Walker et al. discloses extracting PHB by first flocculating the cells by heat or pH treatment then extracting with a suitable solvent, U.S. Pat. No. 4,138,291 to Lafferty discloses bacterial strains assimilating various carbon sources and converting them to PHB, and U.S. Pat. No. 3,121,669 to Baptist shows adding acetic acid vapor to an aerated stream of culture medium for production of PHB.

Although PHB can be produced in large amounts in natural bacterial genera according to the techniques described above, these bacteria are less manipulatable and not as well characterized as *E. coli*. In the field of genetic engineering, a relatively large body of knowledge exists for *E. coli*. *E. coli* have been utilized as host cells for producing a Wide variety of products including Human Growth Hormone, insulin and interferon. In order to make PHB production more regulatable, a need exists for cloning the PHB biosynthetic pathway into *E. coli*.

SUMMARY OF THE INVENTION

It is therefore an object of this invention to clone and express in *E. coli*, the *A. eutrophus* H16 PHB biosynthetic pathway.

According to the invention, experiments have been performed for cloning the PHB biosynthetic pathway found in *A. eutrophus* H16 into *E. coli* and expressing that pathway by the production of PHB in the cloned *E. coli*. An *A. eutrophus* H16 library was constructed using cosmid pVK102. Cosmid clones that encoded the PHB biosynthetic pathway were sought by assaying for beta-ketothiolase. Six enzyme positive clones were identified and three of these clones manifested acetoacetyl CoA reductase activity and accumulated PHB. PHB was produced in the cosmid clones at approximately 50% of the level found *A. eutrophus*. One cosmid clone was subjected to subcloning experiments, and the PHB biosynthetic pathway was isolated on a 5.5 kilobase (kb) KpnI-EcoRI fragment. This fragment, when cloned into small multicopy vectors, can direct the synthesis of PHB in *E. coli* to levels approaching 80% of the bacterial cell dry weight.

BRIEF DESCRIPTION OF THE DRAWINGS

The foregoing and other objects, aspects and advantages of the invention will be better understood from the following detailed description of the preferred embodiments of the invention with reference to the accompanying drawings, in which:

FIG. 2 is a table showing the analysis results of cosmid clones for enzyme activity and PHB accumulation;

FIG. 4 is a table showing the analysis results of subclones for enzyme activity and PHB production;

DETAILED DESCRIPTION OF THE PREFERRED EMBODIMENTS OF THE INVENTION

Figure 1:
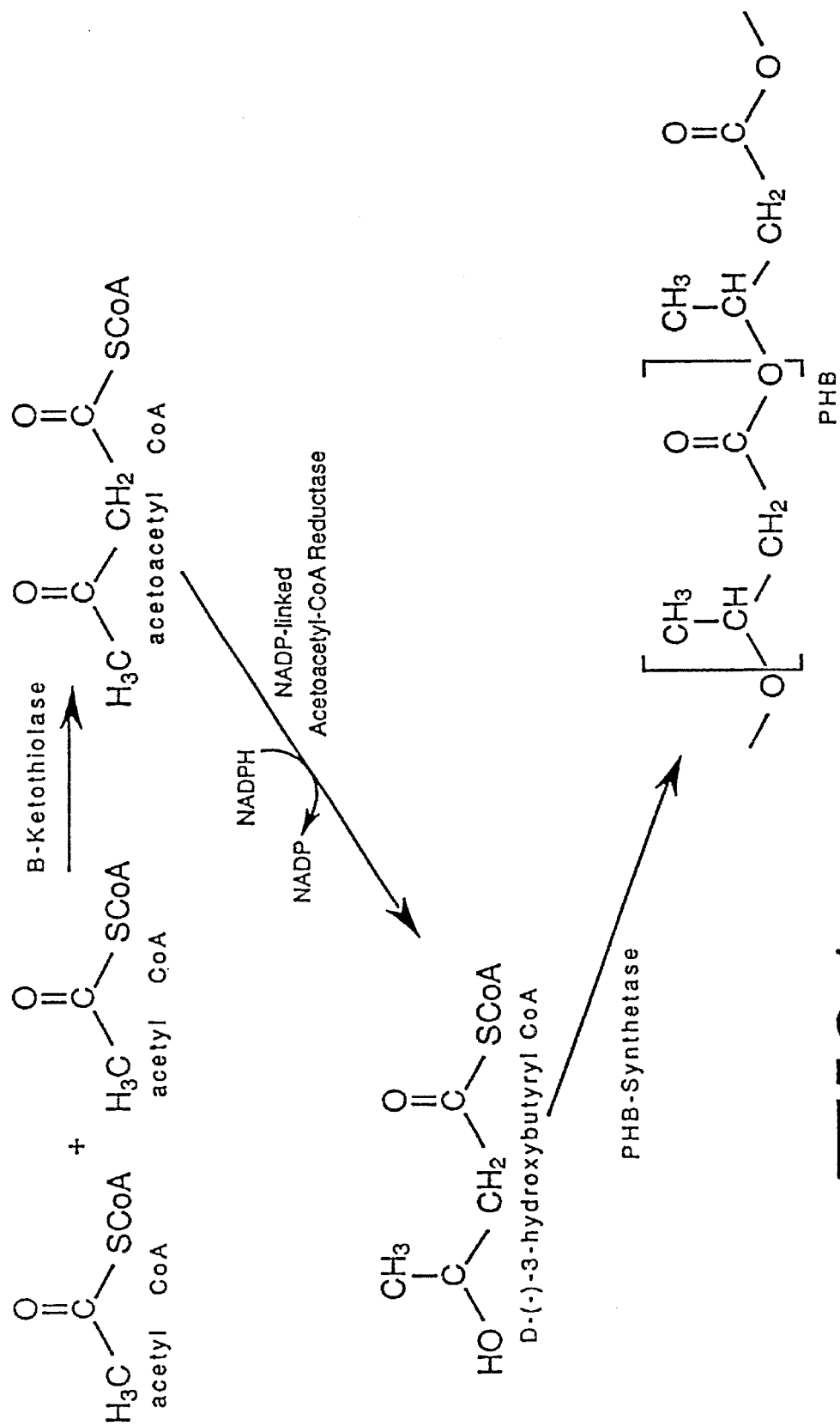
FIG. 1 is a chemical reaction sequence showing the synthesis of PHB.

Experiments have been conducted which include the cloning of the PHB biosynthetic pathway and the production of PHB in *E. coli* to a high internal concentration. All chemicals used in the experiments were reagent grade and were obtained from the Sigma Chemical Company of Missouri or from United States Biochemicals of Ohio. *A. eutrophus* H16, *E. coli* LE392, and *E. coli* DH1 were obtained from the American Type Culture Collection (ATCC) of Maryland. *E. coli* DH5 was obtained from the Bethesda Research Laboratories. Luria Broth (LB) and antibiotics were prepared according to the methods described in Maniatas et al., *Molecular Cloning: a laboratory manual*, Cold Spring Harbor Laboratory, New York, 1982. The cosmid pVK102 was obtained in *E. coli* HB101 from the ATCC.

(1) Generation and Initial Screening of the *A. eutrophus* H16 Library.

A cosmid library of *A. eutrophus* H16 total DNA was constructed by inserting 20-kb to 25-kb DNA fragments in pVK102, followed by transduction of *E. coli* LE392. Total *A. eutrophus* H16 DNA was extracted by the sarcosyl lysis method described in Pritchard et al., *Basic cloning techniques: a manual of experimental procedures*, Blackwell Scientific Publications, London, 1985. A series of partial Sal I restriction endonuclease digests of the DNA was conducted in order to determine the reaction conditions that would yield the maximum percentage of DNA fragments in the 20-kb to 25-kb range. By using the parameters obtained from the calibrating reaction, a large scale digest was performed and the DNA was purified by phenol extraction and ethanol precipitation. The cosmid pVK102 was extracted according to the method of Hansen and Olsen described in "Isolation of large bacterial plasmids and characterization of the P2 incompatibility group plasmids pMG1 and pMG5", *J. Bacteriol.*, 135:227–238, 1978. The cosmid pVK102 was then purified in a cesium chloride (CsCl) gradient, digested with Sal I, and purified by phenol extraction and ethanol precipitation. The partially digested genomic DNA fragments and the cosmid were mixed at an insert-to-vector molar ratio of 20:1 at a final total NA concentration of 400µg/ml, and the mixture was subjected to ligation overnight at 14° C. Part of the ligation was packaged by using the Promega Packagene kit, available from Promega Biotec of Wisconsin, and the packaged cosmids were used to transform *E. coli* LE392. The bacteria were plated onto plates of LB plus kanamycin, and resultant clones were picked for use in the library. Approximately 1,100 clones were picked for further assay. Of these clones, nine percent were polycosmids. Clones were stored individually in LB plus 15% glycerol at −85° C.

The cosmid library was initially screened by assaying for beta-ketothiolase activity. The enzyme assay for beta-ketothiolase (thiolysis reaction) was conducted using the method of Senior et al. described in "Poly-beta-hydroxybutyrate biosynthesis and the regulation of glucose metabolism in *Azotobacter beijerinkii*" *Biochem. J.*, 125:55–68, 1971, and "The regulation of poly-beta-hydroxybutyrate metabolism in *Azotobacter beijerinkii*" *Biochem J*, 134:225–238, 1973 Cell extracts were prepared for enzyme assay according to the following procedures: one milliliter of an overnight culture in LB was pelleted by centrifugation in a microcentrifuge for one minute; the supernatant was removed, and the pellet was resuspended in 200 µl of breaking buffer which was comprised of 20 mM potassium phosphate buffer at pH 7.2, 5 mM magnesium chloride ($MgCl_2$), 1 mM ethylenediaminetetraacetic acid (EDTA), 1 mM dithiothreitol, and 1M glycerol; the suspension was subjected to sonication using an Artek 300 sonicator with a microprobe at the maximum setting wherein sonication consisted of four fifteen second bursts; the sonic extract was subjected to centrifugation in a microcentrifuge for five minutes; and the supernatatant was transferred to a different microcentrifuge tube on ice for analysis. For assays done at later times, the cells were pelleted by centrifugation in a microcentrifuge at room temperature for one minute, the supernatant was removed and the pellets were stored at −85° C. until assay, at which time the pellets were resuspended and sonicated as described above.

In the beta-ketothiolase activity test, positive activity was measured in terms of micromoles of acetoacetyl-CoA degraded per minute per milligram of protein. Note that the reaction was assayed in the reverse direction but that one could also assay for acetoacetyl-CoA produced. To facilitate screening, 5 ml cultures of each clone were grown and then pooled in groups of five for assay. FIG. 2 shows that beta-ketothiolase activity was measurable in *A. eutrophus*, but not in *E. coli* LE392 lysates which had been cleared of particulate matter. Of the more than two hundred pools that were screened, six were positive for beta-ketothiolase activity. Individual clones from each pool were screened, and activity was traced to six clones which are identified in the table of FIG. 2. The activities of the beta-ketothiolase-positive recombinants ranged between 50 and 15% of that found in *A. eutrophus* H16 (FIG. 2 shows the results from a single run of a series of six runs and the 50% figure was determined from the series of six runs).

(2) Screening of the beta-ketothiolase-positive recombinants.

The six recombinant clones which were positive for beta-ketothiolase activity were further screened by assaying for acetoacetyl-CoA reductase activity and by monitoring PHB accumulation. The enzyme assay for acetoacetyl-CoA reductase was conducted according to the methods covered in the Senior et al. article noted above. Acetoacetyl-CoA reductase activity was measured in terms of micromoles of NADPH oxidized per minute per milligram of protein. Protein was measured using the Bio-Rad® protein assay available from the Bio-Rad Laboratories of California. The PHB accumulation assay was done according to the method of Ward and Dawes in "A disk assay for poly-beta-hydroxybutyrate", *Anal. Biochem.*, 52:607–613, 1973, except that Whatman GF/F filters were used instead of Whatman GF/A filters. PHB amounts were calculated from a standard curve by using known quantities of DL-hydroxybutyrate.

FIG. 2 shows that three recombinant clones, which harbor cosmids pAE65, pAE175, and pAE689, respectively, were positive for acetoacetyl-CoA reductase activity and PHB production. The clone harboring pAE65 expressed acetoacetyl-CoA reductase activity to a much higher level than did *A. eutrophus* H16 but produced a very small amount of PHB. Conversely, acetoacetyl-CoA reductase activity in clones harboring pAE175 and pAE689 was extremely low when compared to that of *A. eutrophus* H16, but both clones produced PHB to approximately 50% of the concentration achieved in *A. eutrophus* H16. It is believed that the low reductase activity and high PHB production exhibited by clones harboring pAE175 and pAE689 is the norm and that pAE65 reductase activity is an artifact which results from scrambling of the DNA fragments in the cloning process. The fact that restriction digest patterns of pAE175 and pAE689 were quite similar, and the restriction digest pattern of pAE65 was quite different provides support for this belief.

(3) Subcloning of pAE175 fragments.

Figure 3:
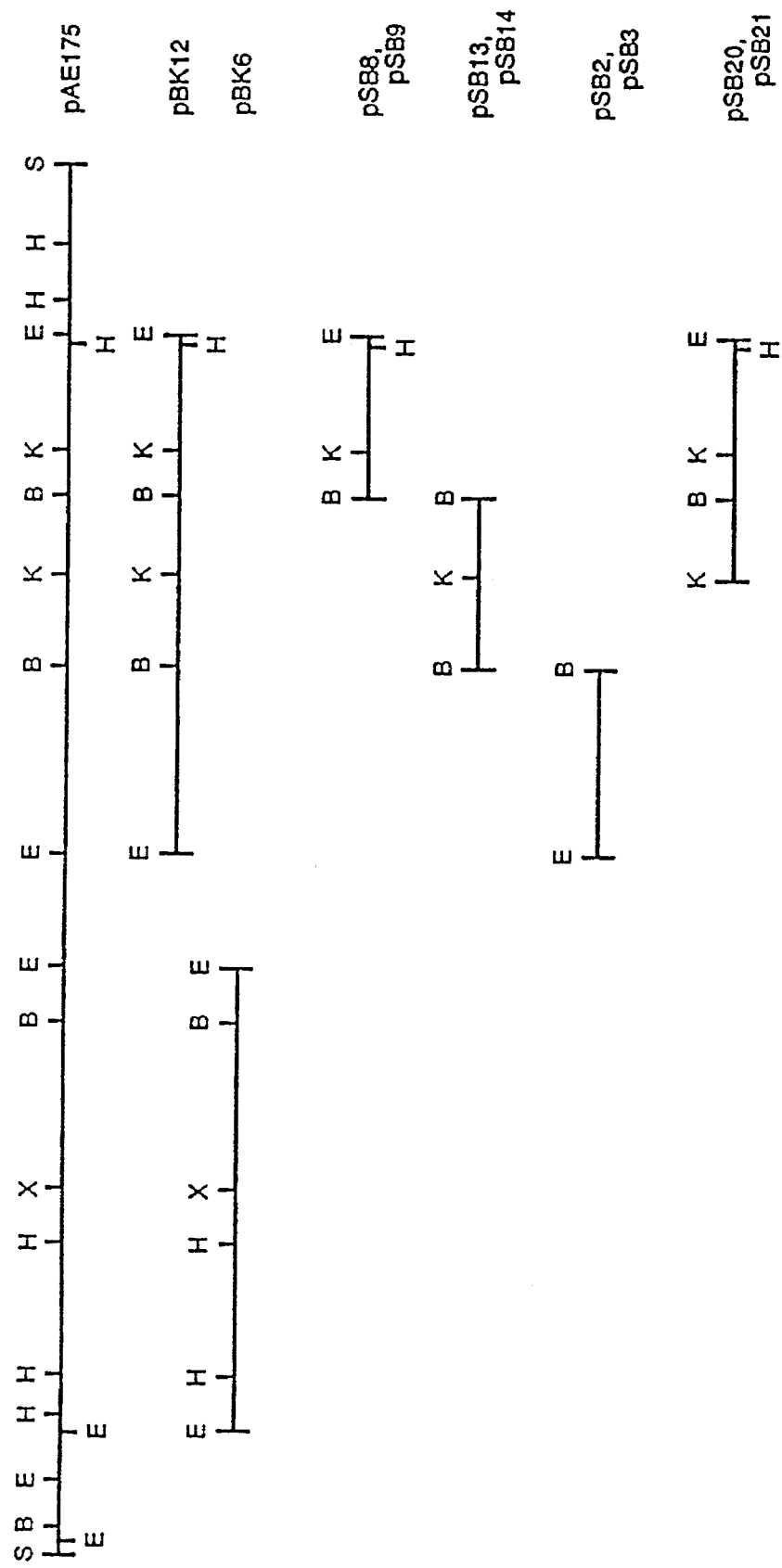
FIG. 3 is a restriction endonuclease map of the cosmid pAE175 insert showing subcloned restriction fragments.

FIG. 3 shows a restriction endonuclease map of the pAE175 cosmid DNA insert. Two central EcoRI fragments were subcloned into the plasmid pUC13, a plasmid available from Pharmacia. Subcloning of the cosmid and plasmid DNA fragments was performed according to the following procedures: recombinant cosmids were purified according to method of Hansen and Olsen described in "Isolation of large bacterial plasmids and characterization of the P2 incompatibility group plasmids pMG1 and pMG5", *J. Bacteriol.*, 135:227–238, 1978; the purified recombinant cosmid was digested with the appropriate restriction endonuclease; and the fragments to be melted were isolated in low-melting temperature agarose as described in Burns, "A method for the ligation of DNA following isolation from low melting temperature agarose", *Anal. Biochem.*, 135:48–51, 1983. Ligation reactions contained plasmids and insert DNA at a 1:3 ratio, respectively. Restriction enzymes and T4 DNA ligase were purchased from Bethesda Research Laboratories of Maryland or from United States Biochemicals. Seakem GT agarose, available from the FMC Corp., Marine Colloids Division, of Maine, was used as the agarose.

Two clones, harboring pBK12 and pBK6 EcoRI restriction fragments, respectively, were picked and analyzed for beta-ketothiolase activity, acetoacetyl-CoA reductase activity, and PHB production. FIG. 4 shows an analysis of subclones for enzyme activity and PHB production where, interestingly, high beta-ketothiolase activity was detected in both clones. However, acetoacetyl-CoA reductase activity and PHB production was only detected in clones harboring pBK12. The pBK12 insert is approximately 14 kb in length. As in clones harboring pAE175 and pAE689, the acetoacetyl-CoA reductase activity in the clone harboring pBK12 was found in lower amounts than in *A. eutrophus*. PHB production in the pBK12 harboring clone was lower than that found in the PHB producing cosmid clones.

It is known that the PHB pathway has a biosynthetic portion and a degradative portion and is made up of five enzymes. In Dawes et al., "The role and regulation of energy reserve polymers in microorganisms", *Adv. Microb. Physiol.*, 14:135–266, 1973, it is pointed out that beta-ketothiolase is both the entry and exit point of the cycle. The existence of two beta-ketothiolase activities raises the possibility that the activity found on pBK12 is part of the biosynthetic portion while the activity found on pBK6 is part of the catabolic portion. To test the possibility that pBK6 contained part or all of the biodegradative pathway, the clone was assayed for two of the remaining three catabolic enzymes, D-3-hydroxybutyrate and succinyl-CoA transferase. The enzyme assays were performed according to the methods of Senior et al. noted above. Neither activity was found in lysates of *E. coli* harboring pBK6, *E. coli* harboring pBK12, or *E. coli* harboring pAE175, whereas both activities were easily measured in *A. eutrophus* H16. Therefore, the beta-ketothiolase activity On pBK6 is unexplained; however, there is a possibility that the three remaining catabolic enzymes are simply not proximal to the beta-ketothiolase activity.

Plasmid pBK12 was further subcloned by digesting it with EcoRI and BglII. Two EcoRI-BglII fragments and one BglII fragment were obtained and each fragment was approximately 4 kb in length. Six subclones, representing each portion of the pBK12 insert in duplicate, were picked and assayed for beta-ketothiolase activity, acetoacetyl-CoA reductase activity, and PHB accumulation, as described above. FIG. 4 shows beta-ketothiolase activity and acetoacetyl-CoA reductase activity were detected in *E. coli* harboring plasmids pSB8 and pSB9. FIG. 3 shows the *E. coli* harboring plasmids pSB8 and pSB9 as the right most BglII-EcoRI fragment. The activities expressed in pSB8 and pSB9, shown in FIG. 4, are considerably higher than those expressed in *A. eutrophus*.

The data from analyses of pSB8 and pSB9 were interpreted to mean that the first two enzymes of the PHB biosynthetic pathway are located on the 3,500 base BglII-EcoRI fragment, but that the third enzyme, PHB synthetase, was either cleaved by BglII or is positioned to the left of the BglII site. To obtain the whole pathway on a sequence small enough to use in DNA sequence studies, a 5.5 kb KpnI-EcoRI fragment was cloned into pUC18, a plasmid obtained from Bethesda Research Laboratories of Maryland. Two clones harboring pSB20 and pSB21 were tested and both clones exhibited beta-ketothiolase activity, acetoacetyl-CoA reductase activity and PHB production. FIG. 4 shows the subclones pSB20 and pSB21 accumulated nearly as much or more PHB as *A. eutrophus* H16. FIG. 3 shows a restriction endonuclease map of the pSB20 and pSB21 fragments relative to the pAE175 cosmid insert.

(4) Comparison of *A. eutrophus* H16 DNA with cloned DNA.

Figure 5:
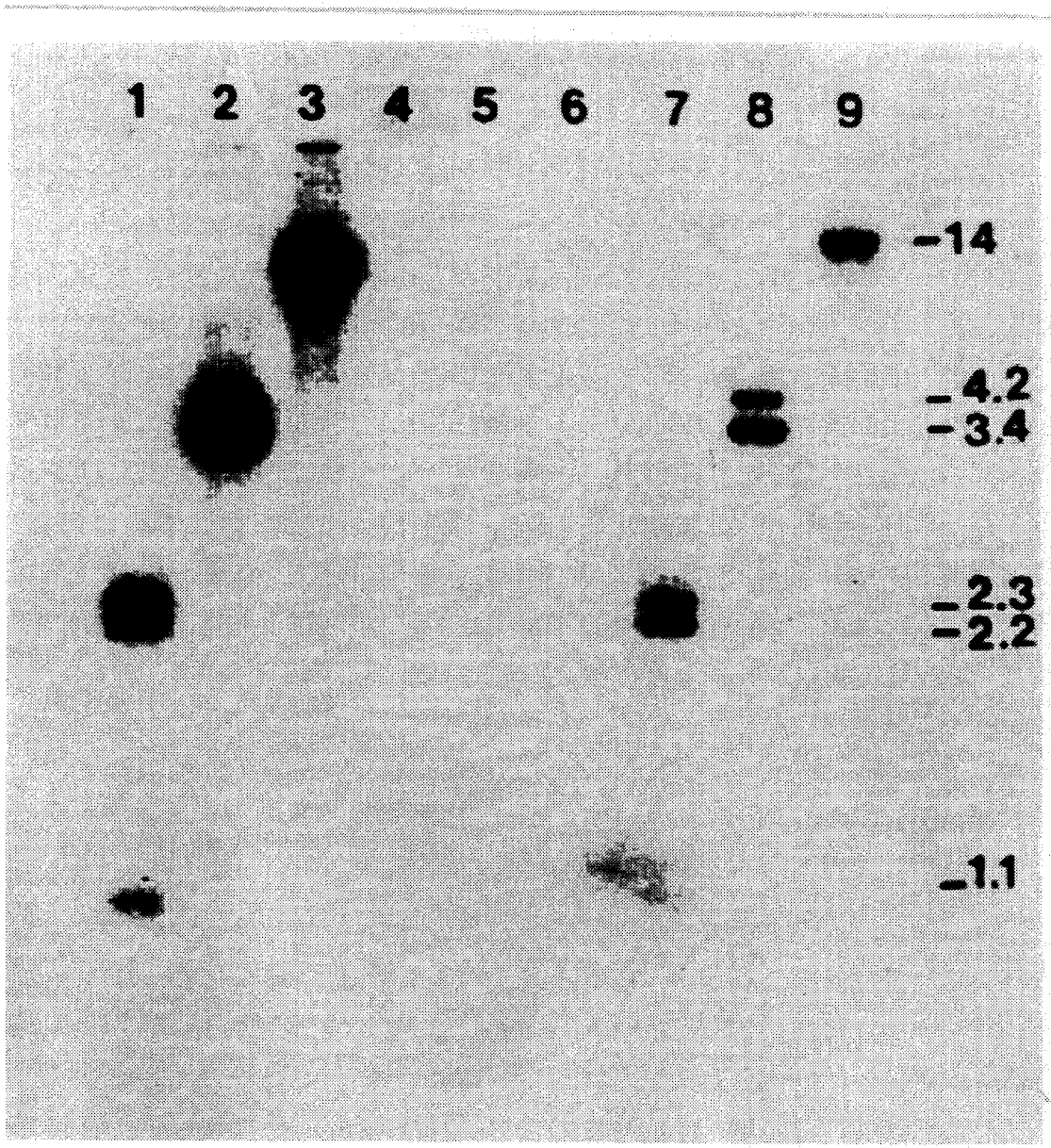
FIG. 5 is a Southern blot analysis of DNA from *E. coli* harboring pAE175, *E. coli* harboring LE392 and *A. eutrophus* H16 genomic DNA.

Because the manner in which the PHB pathway was cloned left open the possibility that the cloned fragment was a product of scrambling, Southern blot analysis was performed to demonstrate that the PHB biosynthetic pathway in *A. eutrophus* H16 has the same restriction pattern as that of the cloned PHB DNA. Southern blot analysis was performed by the method of Maniatis et al. in *Molecular cloning: a laboratory manual*, Cold Spring Harbor Laboratory, New York. The probe was made radioactive by using a random primer extension kit obtained from DuPont, NEN Research Products, of Massachusetts. Digested pAE175 was compared to digests of DNA extracted from *A. eutrophus* H16 and *E. coli* LE392. Restriction endonucleases used were EcoRI, EcoRI-BglII, and SalI, respectively. A gel purified 5.2 kb PHB fragment was labeled and used as a probe. FIG. 5 reveals that the PHB biosynthetic pathway is located on a 14 kb EcoRI fragment in *A. eutrophus* H16 (shown in lane 7) and in pAE175 (shown in lane 1). No hybridization could be detected to any DNA fragments to *E. coli* LE392 (lanes 4 through 6). Further digests of pAE175 and *A. eutrophus* genomic DNA manifested the same restriction patterns, indicating that the cloned PHB biosynthetic pathway was the same as that found in *A. eutrophus* H16.

(5) PHB in *E. coli*.

Figure 6A:
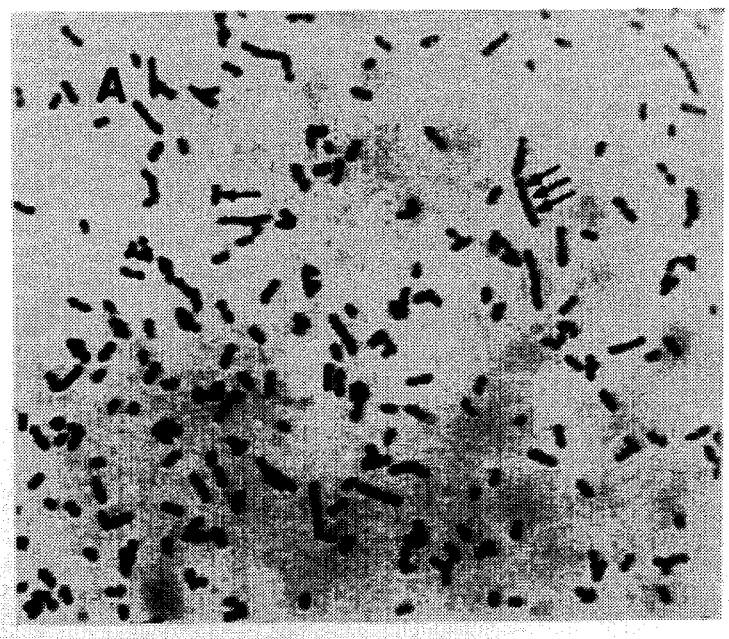
FIGS. 6a and 6b are photomicrographs of *A. eutrophus* H16 and *E. coli* harboring pSB20, respectively, showing intracellular PHB granules.
Figure 6B:
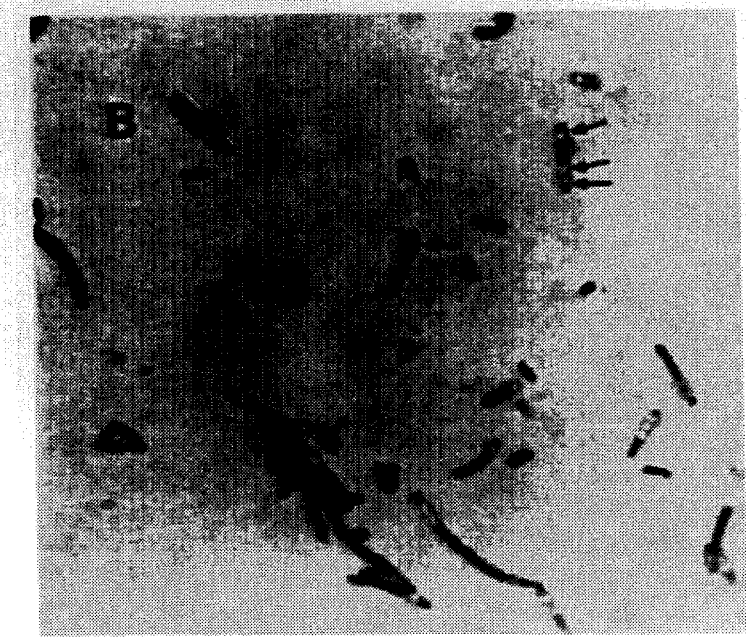

FIGS. 6a and 6b show that PHB is produced in granules in both *A. eutrophus* H16 and *E. coli* harboring the pSB20 plasmid insert. Twenty four hour cultures of *A. eutrophus* H16 and *E. coli* harboring pSB20 were stained for fifteen seconds with crystal violet. The crystal violet is absorbed by the cells, but PHB granules are refractile to the stain. The cultures were examined under an oil immersion lens. FIG. 6a shows PHB granules in A. eutrophus are evident as fuzzy, non-staining areas between stained regions of the bacterium. FIG. 6b shows PHB granules in E. coli much more distinctly. Granule formation in E. coli appears to differ from that in A. eutrophus H16 in that the granules in E. coli were more numerous and were often larger in diameter than the cell. PHB granules in A. eutrophus H16 did not usually distend the cell membrane.

Figure 7:
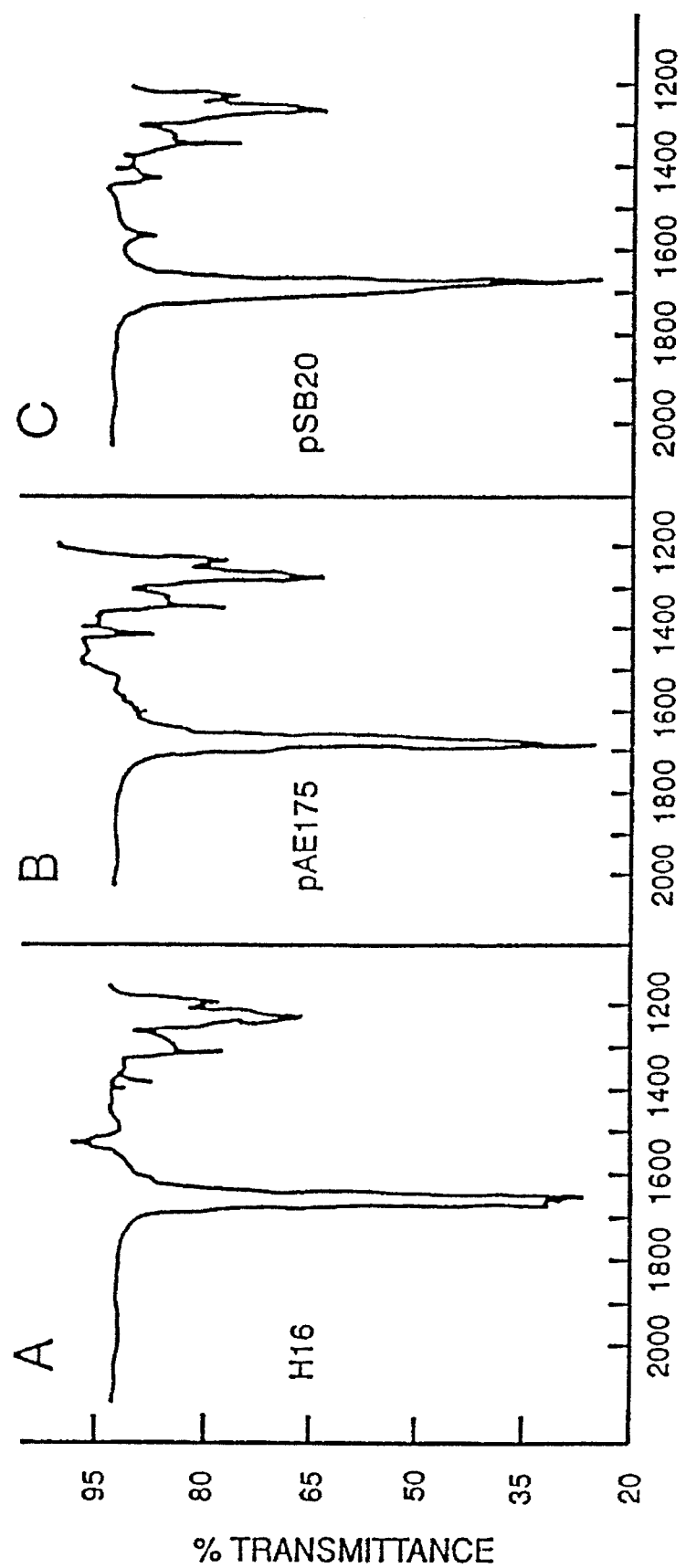
FIG. 7 is a graph showing infrared (IR) spectra of PHB extracted from *A. eutrophus*, *E. coli* harboring pAE175, and *E. coli* harboring pSB20.

FIG. 7 shows IR spectra of PHB which was extracted from A. eutrophus (A), E. coli harboring pAE175 (B), and E. coli harboring pSB20 (C). The infrared (IR) spectra of various PHB samples was obtained utilizing the technique described in Wakisaka, "Formation of crystallin g-endotoxin or poly-beta-hydroxybutyrate acid granules by asporogenous mutants of Bacillus thuringiensis", Appl. Environ. Microbiol., 43:1473–1480, 1982. The results demonstrate that the PHB produced in its native state, i.e., in A. eutrophus H16, and PHB produced in the transformed E. coli, i.e., E. coli harboring pAE175 and E. coli harboring pSB20 have virtually identical IR spectra. In addition, the PHB spectra shown in FIG. 7 are very similar to those from other organisms as indicated in Fernandez-Casillo et al., "Accumulation of poly-beta-hydroxybutyrate by halobacteria", Appl. Environ. Microbiol., 51:214–216, 1986, and in Senior et al., "The regulation of poly-beta-hydroxybutyrate metabolism in Azotobacter beijerinkii" Biochem. J, 134:225–238, 1973

(6) Production of PHB.

Experimental results showed that E. coli harboring both pAE175 and pAE689 cosmid clones produced PHB to approximately 50% of the level achieved in A. eutrophus H16 while expressing reductase levels that were less than 2% of reductase levels in A. eutrophus H16. Substantial levels of intracellular PHB were accumulated in E. coli. These levels approached 90% of the bacterial cell dry weight in some subclones, and PHB was observable as large intracellular bodies. The high levels of expression obtained implies either a high degree of transcriptional versatility or a high degree of transcriptional homology.

PHB has been grown in E. coli harboring the PHB pathway under non-conductive conditions, i.e., a flask of LB is innoculated with the E. coli harboring the PHB biosynthetic pathway and the E. coli are grown in the presence of 1% glucose (where glucose acts as the carbon source for PHB production). However, since the PHB biosynthetic pathway functions like a regulon, PHB production may be controlled in a manner similar to that found in A. eutrophus H16. The inventors have observed that in an oxygen stressed culture, E. coli harboring the PHB biosynthetic pathway have four to five times the enzyme activity and produce twice as much PHB as E. coli harboring the PHB biosynthetic pathway which have not been similarly produced. Therefore, it is assumed that other non-carbon deprivation environments, i.e., nitrogen deprivation, sulfate deprivation, magnesium deprivation, et cetera, will induce higher production of PHB.

A strain of E. coli harboring the PHB biosynthetic pathway which was produced according to the techniques described above has been deposited with the American Type Culture Collection of 12301 Parklawn Drive, Rockville, Md. on Jun. 5, 1989 and bears deposit number: 68006. The strain is like that of PSB20 where the PHB biosynthetic pathway was isolated on a DNA fragment approximately 5.5 kb in length. The advantage of the smaller vector over the larger cosmid clone PAE175 is the ability to produce more copies. Access to the microorganism shall be made available to the public.

While the invention has been described in terms of cloning the PHB biosynthetic pathway from a specific bacterium into E. coli those skilled in the art will recognize that other bacteria produce PHB and that the PHB biosynthetic pathway can be cloned into E. coli in a manner contemplated within the spirit and scope of the appended claims.

Having thus described my invention, what I claim to be new and desire to secure by Letters Patent is the following:

1. An *Escherichia coli* bacterial host transformed by a vector containing a DNA sequence coding for a poly-beta-hydroxybutyrate biosynthetic pathway obtained from *Alcaligenes eutrophus;* wherein the DNA sequence is cloned into a multicopy vector; said *Escherichia coil* bacterial host being capable of expressing said biosynthetic pathway by producing poly-beta-hydroxybutyrate in recoverable quantities of at least about 54% of the bacterial cell dry weight of the *Escherichia coli* bacterial host.

2. The *Escherichia coil* bacterial host as recited in claim 1, where the vector containing the DNA sequence is plasmid pSB20.

3. The *Escherichia coli* bacterial host of claim 1, wherein the poly-beta-hydroxybutyrate is recovered after about a 24 hour period.

4. An *Escherichia coil* bacterial host as recited in claim 1 wherein the vector is a plasmid containing a nucleic acid fragment containing said biosynthetic pathway, said fragment being approximately 5.5 kilobases in length.

5. An *Escherichia coli* bacterial host as recited in claim 1 bearing the following deposit number: ATCC 68006.

6. A method of making poly-beta-hydroxybutyrate comprising the steps of:

culturing an *Escherichia coil* bacterial host transformed by a vector containing a DNA sequence coding for a poly-beta-hydroxybutyrate biosynthetic pathway original from *Alcaligenes eutrophus,* wherein the DNA sequence is cloned into a multicopy vector;

obtaining expression of said poly-beta-hydroxybutyrate biosynthetic pathway in said *Escherichia coli* bacterial host; and recovering said poly-beta-hydroxybutyrate in quantities of about 54% of the bacterial cell dry weight of the *Escherichia coli* bacterial host.

7. The method as recited in claim 6, wherein the vector is plasmid pSB20.

8. The method as recited in claim 6, wherein poly-beta-hydroxybutyrate is recovered after about a 24 hour period.

* * * * *

UNITED STATES PATENT AND TRADEMARK OFFICE
CERTIFICATE OF CORRECTION

PATENT NO. : 5,518,907
DATED : May 21, 1996
INVENTOR(S) : Douglas E. Dennis

It is certified that error appears in the above identified patent and that said Letters Patent is hereby corrected as shown below:

In column 8, line 25, please delete "*coil*" and insert therefor --*coli*--.

In column 8, line 30, please delete "*coil*" and insert therefor --*coli*--.

In column 8, line 36, please delete "*coil*" and insert therefor --*coli*--.

In column 8, line 44, please delete "*coil*" and insert therefor --*coli*--.

Signed and Sealed this

Fifteenth Day of October, 1996

Attest:

BRUCE LEHMAN

*Attesting Officer*     *Commissioner of Patents and Trademarks*